(12) United States Patent
Liu et al.

(10) Patent No.: US 12,721,762 B2
(45) Date of Patent: Sep. 1, 2026

(54) DIAPER ARTICLE WITH MULTIPLE ABSORBENT BODIES

(71) Applicant: The Procter & Gamble Company, Cincinnati, OH (US)

(72) Inventors: Li Liu, Beijing (CN); Wenlu Li, Beijing (CN); Wei Dai, Beijing (CN); Lishuang Peng, Beijing (CN); Jing Zhang, Beijing (CN); Koichi Morimoto, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 324 days.

(21) Appl. No.: 18/407,530

(22) Filed: Jan. 9, 2024

(65) Prior Publication Data

US 2024/0225917 A1 Jul. 11, 2024

(30) Foreign Application Priority Data

Jan. 9, 2023 (WO) ................ PCT/CN2023/071285

(51) Int. Cl.
*A61F 13/505* (2006.01)
*A61F 13/49* (2006.01)
(Continued)

(52) U.S. Cl.
CPC ...... *A61F 13/505* (2013.01); *A61F 13/49011* (2013.01); *A61F 13/4906* (2013.01);
(Continued)

(58) Field of Classification Search
CPC ................ A61F 13/4906; A61F 13/505; A61F 2013/49063; A61F 2013/49065; A61F 2013/5055
See application file for complete search history.

(56) References Cited

U.S. PATENT DOCUMENTS 5,236,428 A * 8/1993 Zajaczkowski ....... A61F 13/474
604/383
5,405,342 A 4/1995 Roessler
(Continued)

FOREIGN PATENT DOCUMENTS

WO 9529655 A1 11/1995

OTHER PUBLICATIONS

AA01547F PCT Search Report and Written Opinion for PCT/CN2023/071285 dated Jun. 5, 2023, 11 pages.
(Continued)

*Primary Examiner* — Catharine L Anderson
(74) *Attorney, Agent, or Firm* — Daniel S. Albrecht

(57) ABSTRACT

Disclosed is an article having an absorbent assembly and an application structure, the absorbent assembly containing: 1) a first absorbent body having a first water permeable topsheet; a first water impermeable backsheet having a transverse dimension T1; a first absorbent core between the first topsheet and the first backsheet; a first outer cover on the garment facing side of the first backsheet; 2) a second absorbent body on the garment facing side of the first absorbent body, having: a second water permeable topsheet having a transverse dimension T3; a second absorbent core; and 3) a chassis on the garment facing side of the second absorbent core, the chassis containing a water impermeable chassis backsheet; wherein T1 is greater than T3, and wherein the first outer cover and the second topsheet are bonded with a Temporary Bond which enables removing the first absorbent body from the diaper article.

14 Claims, 10 Drawing Sheets

(51) Int. Cl.
*A61F 13/515* (2006.01)
*A61F 13/53* (2006.01)
*A61F 13/514* (2006.01)
*A61F 13/84* (2006.01)

(52) U.S. Cl.
CPC ............ *A61F 13/515* (2013.01); *A61F 13/53* (2013.01); *A61F 2013/49065* (2013.01); *A61F 2013/5055* (2013.01); *A61F 2013/5147* (2013.01); *A61F 2013/8497* (2013.01)

(56) References Cited

U.S. PATENT DOCUMENTS 5,460,624 A 10/1995 Ahr et al.
5,599,339 A * 2/1997 Horney ................. A61F 13/474 604/389
5,613,959 A 3/1997 Roessler et al.
5,613,964 A * 3/1997 Grenier ................. A61F 13/505 604/385.01
5,910,137 A 6/1999 Clark et al.
6,096,017 A 8/2000 Osborn, III
6,524,291 B1 2/2003 Bjoerklund et al.
6,579,272 B1 6/2003 Samuelsson et al.
7,264,615 B2 * 9/2007 Sherrod ............ A61F 13/53708 604/385.03
7,938,814 B2 5/2011 Koyama
8,702,673 B1 * 4/2014 Jones .................... A61F 13/505 604/386
10,159,609 B2 12/2018 Kleuskens
10,159,611 B2 12/2018 Kleuskens
2003/0009142 A1 1/2003 Nukina et al.
2003/0100873 A1 5/2003 Hermansson et al.
2003/0163105 A1 * 8/2003 Tears .................... A61F 13/505 604/385.03
2005/0256480 A1 11/2005 La Von
2008/0095978 A1 4/2008 Siqueira et al.
2011/0034893 A1 2/2011 Waxman et al.
2012/0310202 A1 12/2012 Wilson
2017/0216106 A1 8/2017 Kleuskens
2017/0216111 A1 8/2017 Kleuskens et al.
2017/0239099 A1 8/2017 Kleuskens
2020/0315866 A1 10/2020 Fukae et al.
2023/0201048 A1 6/2023 Högberg et al.
2024/0225918 A1 * 7/2024 Liu ................... A61F 13/49006

OTHER PUBLICATIONS

All Office Actions; U.S. Appl. No. 18/407,541, filed Jan. 9, 2024.
Unpublished U.S. Appl. No. 18/407,541, filed Jan. 9, 2024, to Li Liu et. al.

* cited by examiner

DIAPER ARTICLE WITH MULTIPLE ABSORBENT BODIES

CROSS REFERENCE TO RELATED APPLICATION

This application claims priority, under 35 U.S.C. § 119, to PCT Patent Application PCT/CN2023/071285, filed Jan. 9, 2023, the entire disclosure of which is hereby incorporated by reference.

FIELD

The present disclosure relates to diaper articles having multiple layers of absorbent bodies enabling a second usage of the diaper article after removal of one of the absorbent bodies.

BACKGROUND

Diaper articles for personal hygiene, such as disposable taped diapers, disposable pants, and adult incontinence undergarments, are designed to absorb and contain various body exudates, including urine, menses, and fecal matter. Diaper articles having multiple absorbent bodies which enables a second usage after the first soiling are desired. Such diaper article requires having multiple absorbent bodies, wherein the first absorbent body may be removed after the first soiling, and thereby exposing another absorbent body. Such diaper articles having multiple absorbent bodies may provide convenience by enabling removing the soiled absorbent body without complete removal of garments. Such convenience may be particularly desired during outing from the home, or during cold seasons. Diaper articles having multiple absorbent bodies may also provide conservation of material.

Diaper articles having multiple absorbent bodies have been known in the art, such as in U.S. Pat. No. 5,613,959 US 2017/0216111A, US 2017/0216106A, and US 2017/0239099A. While such diaper articles have been known, they may require improvements for actual usage.

For example, those known in the art may not have considerations for delivering sufficient containment, leakage prevention, or wear comfort before and after removal of the first absorbent body. For example, those known in the art may not have practical measures for keeping the absorbent body for second usage intact during the first usage. For example, those known in the art may not have considerations for enabling smooth removal of the first absorbent body from the remainder of the article.

Based on the foregoing, there is a need for a diaper article having multiple layers of absorbent bodies wherein the absorbent body for second usage remains intact during the first usage, while maintaining wear comfort, and enabling smooth removal of the first absorbent body after usage. There is also a need for a diaper article which addresses the concerns of consumers who are conscious about sustainable usage of material.

SUMMARY

The present disclosure is directed to a diaper article comprising an absorbent assembly and an application structure, the absorbent assembly comprising:

1) a first absorbent body comprising:
   a) a first water permeable topsheet;

b) a first water impermeable backsheet having a transverse dimension T1;
   c) a first absorbent core disposed between the first topsheet and the first backsheet;
   d) a first outer cover disposed on the garment facing side of the first backsheet;
2) a second absorbent body disposed on the garment facing side of the first absorbent body, comprising:
   a) a second water permeable topsheet having a transverse dimension T3;
   b) a second absorbent core; and
3) a chassis disposed on the garment facing side of the second absorbent core, the chassis comprising a water impermeable chassis backsheet;

wherein T1 is greater than T3, and wherein the first outer cover and the second topsheet is bonded with a Temporary Bond which enables removing the first absorbent body from the remainder of the diaper article.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1B:
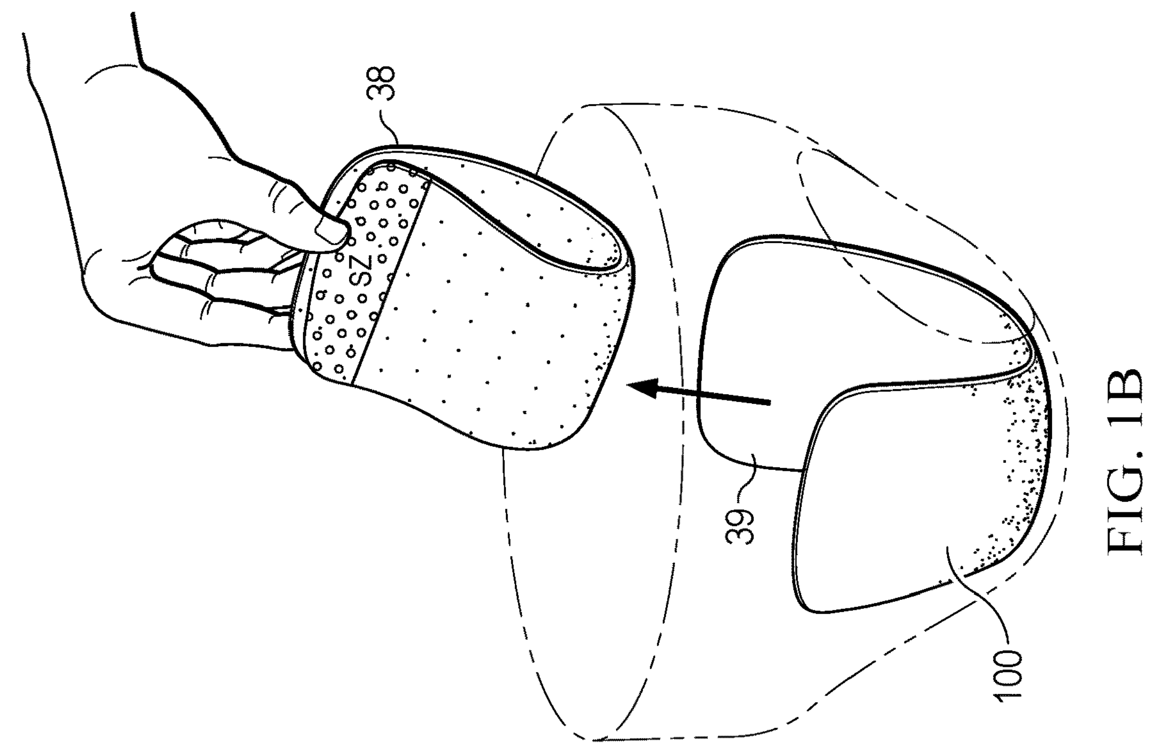
FIG. 1A-1B are schematic perspective views of an embodiment of the diaper article of the present invention showing how the first absorbent body is removed from the remainder of the diaper article.

As used herein, the following terms shall have the meaning specified thereafter:

"Diaper article" refers to articles of wear including an application structure which may be in the form of taped type diapers, pant type diapers, incontinent briefs, feminine hygiene garments, and the like. Diaper articles such as feminine pads which require a separate part for wear, such as a pin, a tape, or an undergarment, is not considered a "diaper article".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Wearer-facing" and "garment-facing" refer respectively to the relative location of an element or a surface of an element or group of elements. "Wearer-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable diaper article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Nonwoven", nonwoven layer" or "nonwoven web" are used interchangeably to mean an engineered fibrous assembly, primarily planar, which has been given a designed level of structural integrity by physical and/or chemical means, excluding weaving, knitting or papermaking (ISO 9092: 2019 definition). The directionally or randomly orientated fibers, are bonded by friction, and/or cohesion and/or adhesion. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yam). Nonwoven webs can be formed by many processes such as meltblowing, spunbonding, solvent spinning, electrospinning, carding and airlaying. The basis weight of nonwoven webs is usually expressed in grams per square meter ($g/m^2$ or gsm).

"Water-permeable" and "water-impermeable" refer to the penetrability of materials in the context of the intended usage of disposable diaper articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Hydrophilic" describes surfaces of substrates which are wettable by aqueous fluids (e.g., aqueous body fluids) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is greater than 90° and the fluid does not spread spontaneously across the surface of the fiber.

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Dimension", "Length", "Width", "Pitch", "Diameter", "Aspect Ratio", "Angle", and "Area" of the article are all measured in a state wherein the article is extended to the Full Stretch Circumference W1 according to the "Whole Article Force Measurement" herein, and utilizing a ruler or a loupe, unless specified otherwise.

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having a L* value of at least 94, an a* value equal to 0±2, and a b* value equal to 0±2 according to the CIE L*a*b* color system.

DETAILED DESCRIPTION

Diaper Article and Absorbent Assembly

Figure 1A:
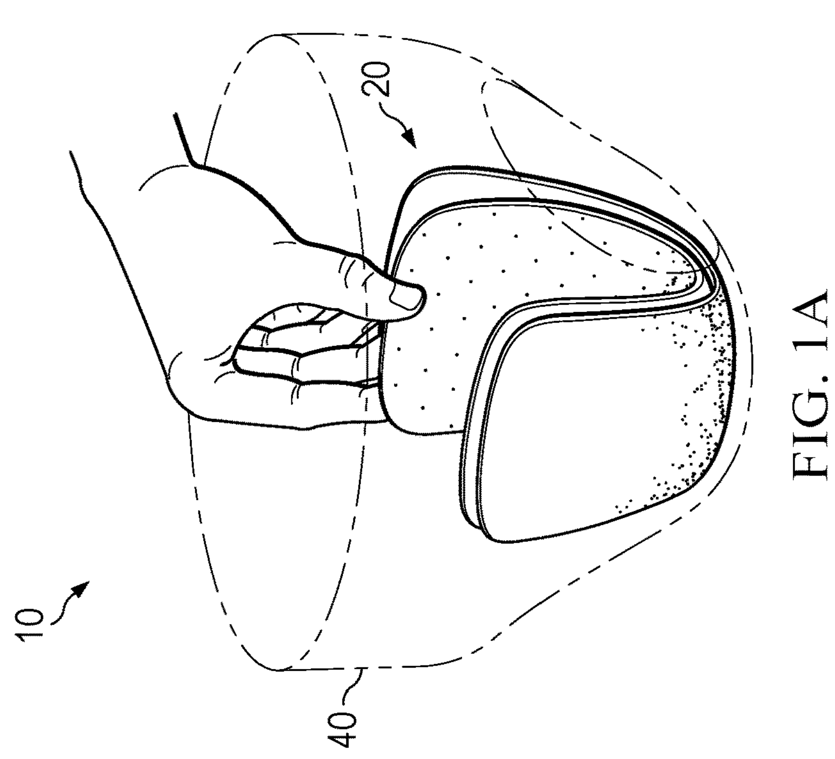

FIGS. 1A-1B are perspective views of an embodiment of the diaper article (10) of the present invention of the pant type comprising an absorbent assembly (20) and an application structure (40). The absorbent assembly (20) comprises a first absorbent body (38), a second absorbent body (39) disposed on the garment facing side of the first absorbent body, and a chassis (100) disposed on the garment facing side of the second absorbent core, wherein the first absorbent body (38) and the second absorbent body (39) is bonded with a Temporary Bond (TB) which enables removing the first absorbent body (38) from the remainder of the diaper article (10). The diaper article (10) of the present invention has multiple layers of absorbent bodies (38, 39), enabling usage of the diaper article (10) more than once. Accordingly, the chassis (100) and the application structure (40) may be used more than once, thus contributing to sustainable usage of material. Further, the first absorbent body (38) may be removed from the remainder of the diaper article (10) without completely removing the diaper article (10) from the wearer, facilitating easy diaper change.

Figure 2A:
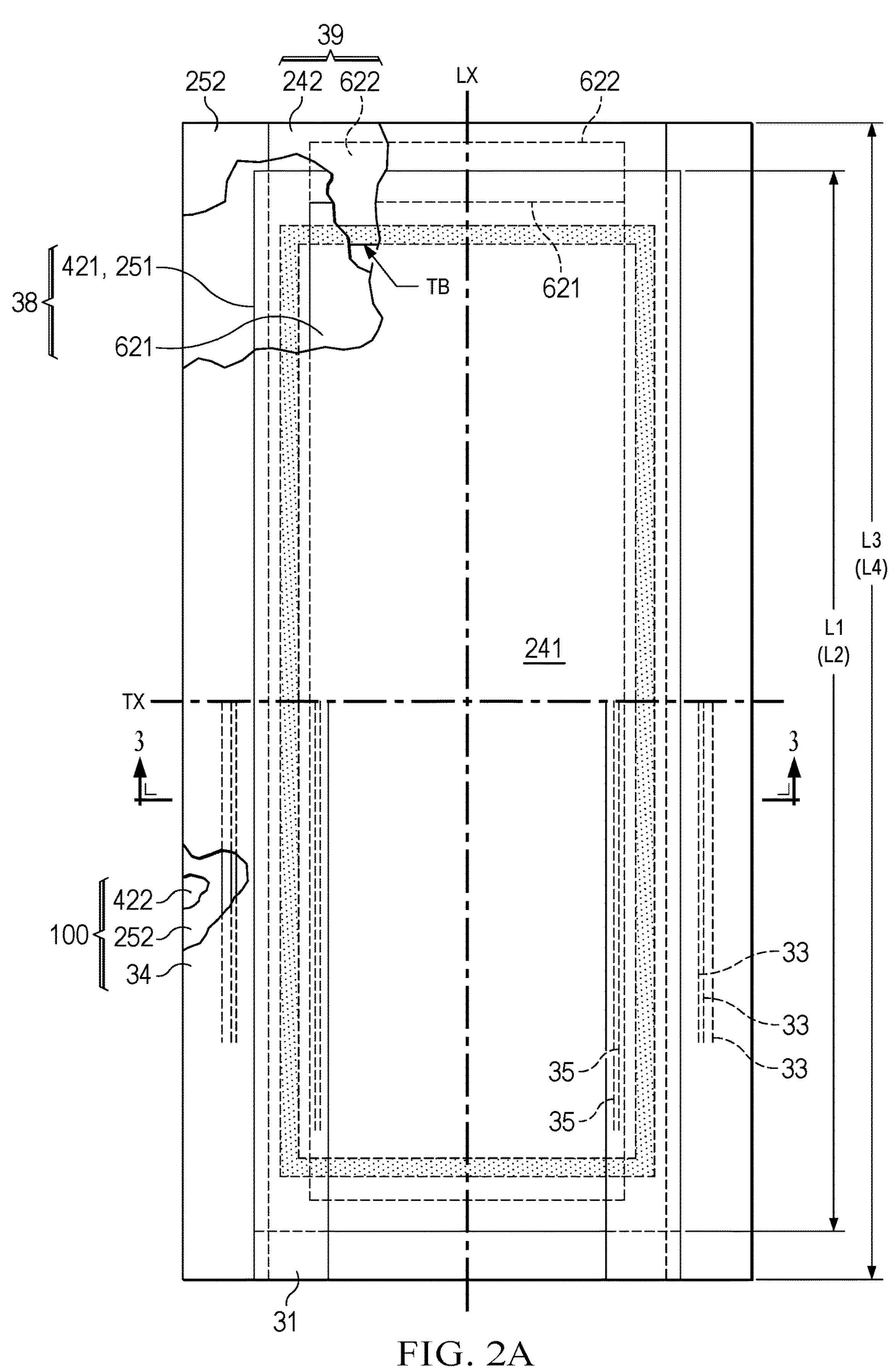
FIG. 2A is a schematic plan view of an embodiment of the absorbent assembly of the present invention showing the wearer-facing side wherein below TX the cuff elements are shown, while above TX the cuff elements are removed.
Figure 2B:
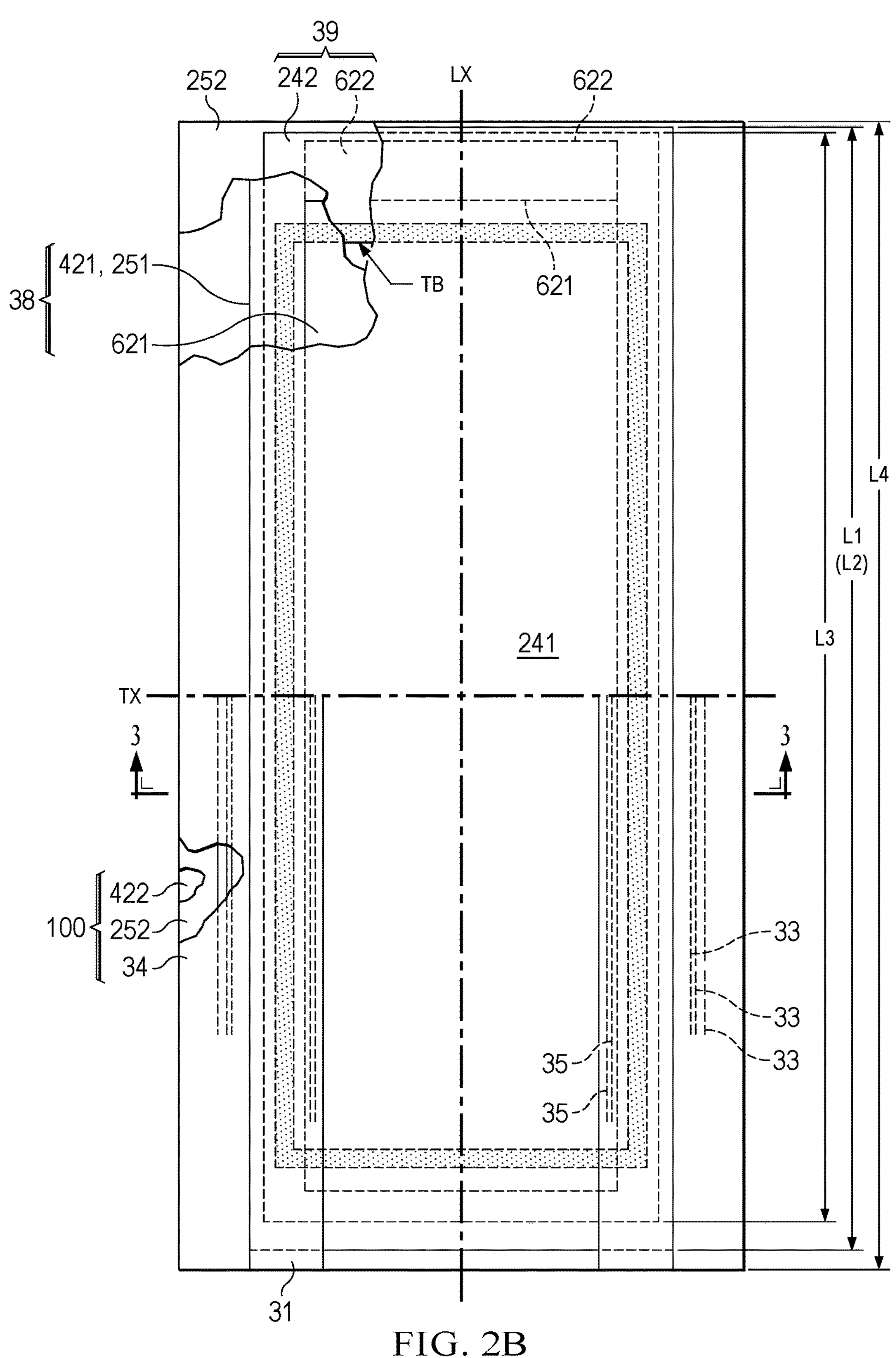
FIG. 2B is a schematic plan view of another embodiment of the absorbent assembly of the present invention showing the wearer-facing side wherein below TX the cuff elements are shown, while above TX the cuff elements are removed.

FIGS. 2A and 2B are schematic plan views of embodiments of the absorbent assembly of the present invention showing the front side on the top and back side on the bottom. The absorbent assembly (20) has a longitudinal centerline LX which also serves as the longitudinal axis, and a transverse centerline TX which also serves as the transverse axis. The figures below TX show the cuff elements, while the figures above TX have the cuff elements removed. Namely, referring to FIG. 3, cuff elements (31, 35, 33, and 34) exist along the left and right transverse edges of the absorbent assembly. These elements are removed in FIGS. 2A and 2B above TX, thus the first topsheet (241) and any elements extending beyond the dimension of the first topsheet (241) are shown. Towards the upper left side of FIGS. 2A and 2B, the elements of the first absorbent body (38) beneath the first topsheet (241) are exposed and shown. Still further, the elements of the second absorbent body (39) beneath the first outer cover (421) are exposed and shown. FIGS. 2A and 2B below TX are shown in a state wherein any elastic cuff elements (33, 35) are fully stretched. Towards the lower left side of FIGS. 2A and 2B, the elements of the chassis (100) beneath the nonwoven forming the chassis outer cuff (34) are exposed and shown.

Figure 3:
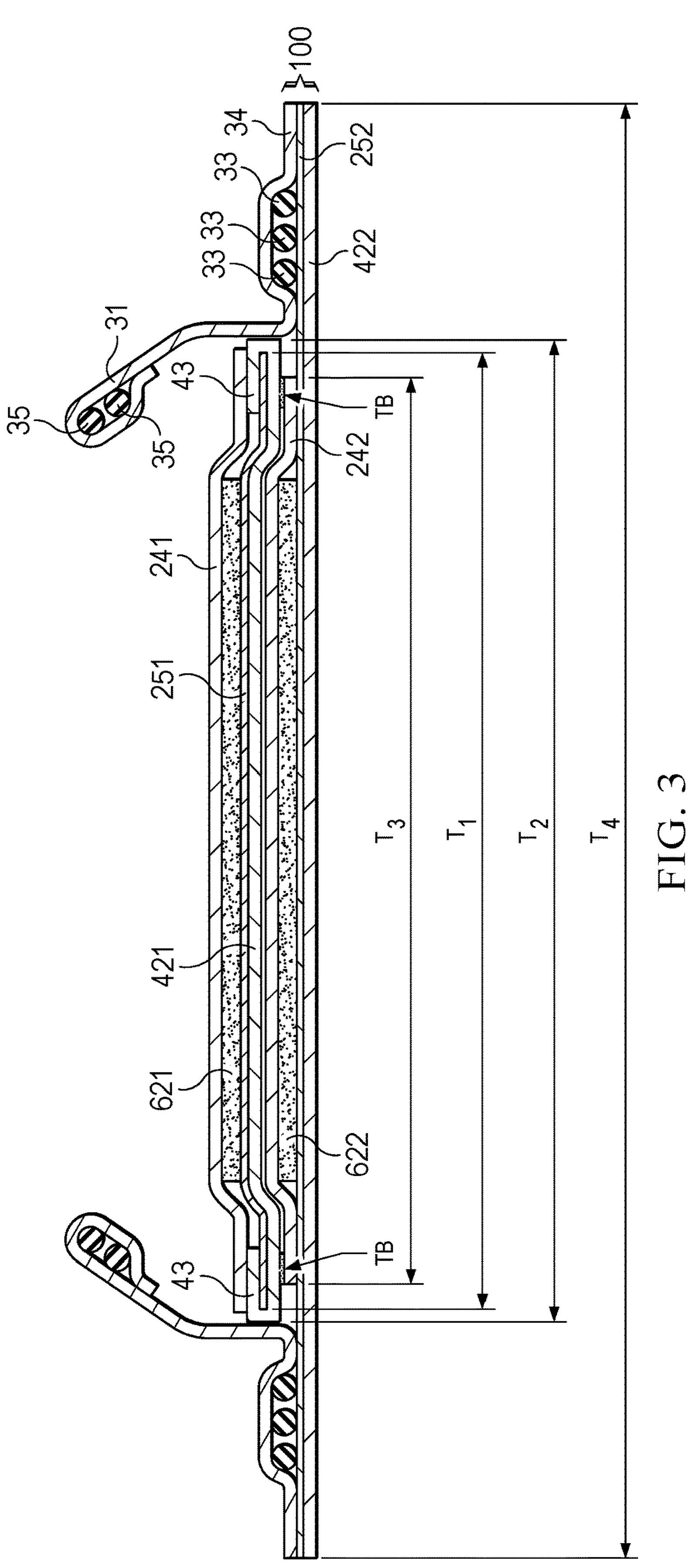
FIG. 3 is a transverse schematic cross section view of either FIG. 2A or 2B taken along line 3-3.

Referring to FIGS. 2A, 2B, and 3, the first absorbent body (38) and the remainder of the diaper article (39, 100) each carry essential components in order to provide the function as an absorbent diaper article (10). Specifically, the first absorbent body (38) comprises a first water permeable topsheet (241), a first water impermeable backsheet (251), a first absorbent core (621) disposed between the first topsheet and the first backsheet, and a first outer cover (421). The first outer cover (421) serves as the interface between the second absorbent body (39) on which the Temporary Bond (TB) is provided. The second absorbent body (39) comprises a second water permeable topsheet (242) and a second absorbent core (622). The second topsheet (242) serves as the interface between the first absorbent body (38) on which the Temporary Bond (TB) is provided. A chassis (100) is disposed on the garment facing side of the second absorbent core, which chassis (100) comprises a water impermeable chassis backsheet (252) which may serve as the barrier to prevent leakage of exudates absorbed by and contained in any absorbent body within the absorbent assembly (20). When there are only first and second absorbent bodies (38, 39), the second absorbent body (39) may be devoid of a second backsheet. When there are more than 2 absorbent bodies, the second absorbent body (39) may further comprise a second backsheet and a second outer cover, the second outer cover serving as the interface between the third topsheet of the third absorbent body on which another Temporary Bond (TB) is provided. In a similar manner, more layers of absorbent bodies may be comprised in the absorbent assembly (20) wherein the absorbent body closest to the garment facing side may be devoid of a backsheet and an outer cover.

Figure 5A:
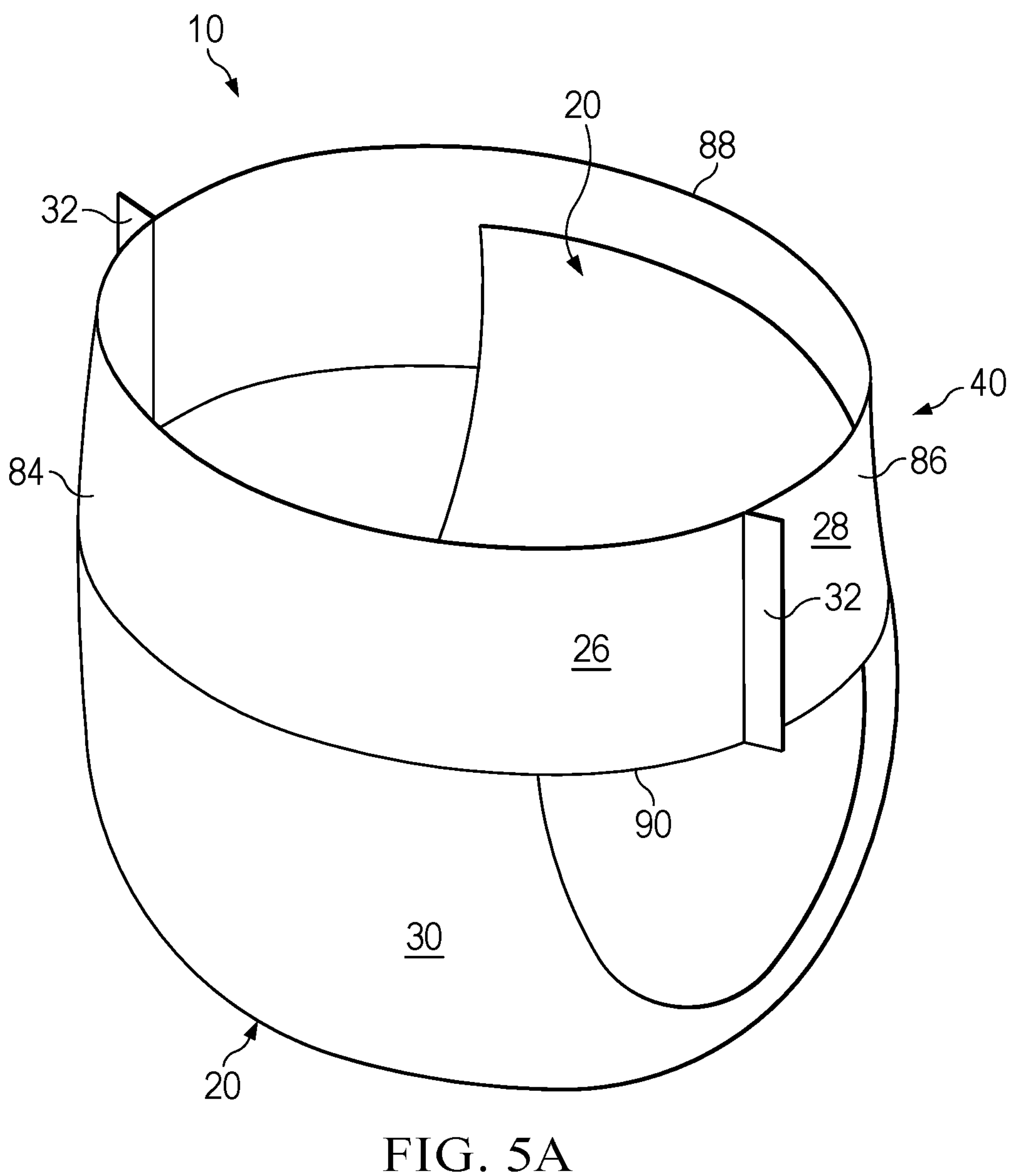
FIG. 5A is a schematic perspective view of one embodiment of a pant diaper article of the present invention.

The absorbent assembly (20) of the present invention may be assembled together with an application structure (40) to form a diaper article (10), wherein the application structure (40) is selected from the group of a fastening structure and an elastic belt (40). Referring to FIG. 5A, the diaper article (10) may take the form of a pant diaper comprising an elastic belt (40), wherein the elastic belt (40) may be formed by nonwoven materials and/or woven materials combined with elastic materials such as elastic bodies and films. While not shown, the diaper article (10) may take the form of a taped diaper comprising a fastening structure. Fastening structures may be, for example, a pair of elongate members and a receiving member, the elongate members transversely protruding from the left and right transverse edges of the back region and fastenable with the receiving member disposed on the front region.

Whether in the pant type or taped type, the diaper article (10) of the present invention, while enabling more than one usage, has an appropriate thickness and thereby are comfortable to wear. The diaper article (10) of the present invention may have a Folded Thickness of no greater than about 12.5 mm according to the measurement herein. By providing the diaper article within such Folded Thickness, the article provides the aesthetic and tactile senses similar to that of a diaper article with a single absorbent body.

Topsheet, Backsheet, and Outer Cover

Referring to FIGS. 2A, 2B, and 3, the absorbent bodies (38, 39) of the present invention each comprise a water permeable topsheet (241, 242) that may be positioned at least in partial contact or close proximity to a wearer. The same or different material may be used for the first and second absorbent bodies (38, 39). Suitable topsheets (241, 242) may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet (241, 242) is generally supple, soft feeling, and non-irritating to a wearer's skin. The topsheet (241, 242) is liquid permeable, permitting bodily fluids to readily penetrate through the thickness of the topsheet (241, 242). Exemplary topsheets (241, 242) suitable herein include those available from Xiamen Yanjan New Material Co. Ltd made of carded nonwoven substrate comprising PE/PET bi-component fibers, Fibertex NiLai, Malaysia with tradename H30501221 or FQN Hazlet NJ with tradename SB1206169. Any portion of the topsheet (241, 242) may be coated with a lotion or skin care composition as is known in the art. Examples of suitable lotions include those described in U.S. Pat. Nos. 5,607,760; 5,609,587; 5,635,191; and 5,643,588.

The first absorbent body (38) and the chassis (100) of the present invention each comprise a water impermeable backsheet (251, 252) which is designed to prevent the exudates absorbed by and contained within the absorbent core (621, 622) from soiling articles that may contact the diaper article (10), such as bed sheets and undergarments. The same or different material may be used for the first absorbent body (38) and the chassis (100). The backsheets (251, 252) may be positioned such that it extends beyond the absorbent core (621, 622) disposed on the wearer-facing side of the particular backsheet (251, 252) in both the longitudinal direction and the transverse direction. Suitable backsheet (251, 252) materials include films such as those manufactured by Plaster Argentina with tradename PLBA NBBS 10-12GSM PR VI. Other suitable backsheet (251, 252) materials may include breathable materials that permit vapors to escape from the diaper article (10) while still preventing exudates from passing through the backsheet (251, 252). Exemplary breathable materials may include materials such as woven webs, nonwoven webs, composite materials such as film-coated nonwoven webs, and microporous films such as manufactured by Daika Japan with tradename MPF DKH-180 15G V7 and manufactured by Berry Nashville, TN with trademark BR-137P V13. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet including, but not limited to, surface treatments, particular film selections and processing, particular filament selections and processing, etc.

The first absorbent body (38) comprises a first outer cover (421) which serves as the interface between the second absorbent body (39). The first outer cover (421) may be made of a soft, non-woven material. The first outer cover (421) and the first backsheet (251) may be joined together by adhesive or any other suitable material or method. An optional chassis outer cover (422) may also be provided on the garment-facing side of the chassis backsheet (252) for providing the diaper article in a finished appearance. Exemplary outer covers (421, 422) suitable herein include those available from Guanhe Hygiene Products Co., Ltd with tradename S31921A made of spunbond nonwoven substrate comprising PP fiber, and Fibertex NiLai Malaysia with tradename A10160EJ—MALAYSIA and available from FQN Hazlet NJ with tradename SM1104174.

Absorbent Core

Referring to FIGS. 2A, 2B, and 3, the absorbent bodies (38, 39) of the present invention each comprise an absorbent core (621, 622) for absorbing and containing body exudates disposed on the wearer facing side. The absorbent cores (621, 622) may include an absorbent layer and an acquisition system. The absorbent layer is the region wherein absorbent materials having a high retention capacity, such as superabsorbent polymers, are present. The absorbent layer may be substantially cellulose free. Alternatively, the absorbent layer may contain cellulose. There may be an absorbent layer mainly comprising cellulose, and another absorbent layer mainly comprising superabsorbent polymers.

Superabsorbent polymers of the absorbent layer may be disposed between first and second layers of material immobilized by a fibrous layer of thermoplastic adhesive material. The first and second layers of materials may be nonwoven fibrous webs including synthetic fibers, such as mono-constituent fibers of PE, PET and PP, multiconstituent fibers such as side by side, core/sheath or island in the sea type fibers. Such synthetic fibers may be formed via a spunbonding process or a meltblowing process. Some portions of the absorbent layers may be configured to have substantially no absorbent material to form a channel or a plurality of channels. Channels may be useful for allowing the absorbent core (621, 622) to bend upon swelling with fluids, such that the crotch region conforms to the wearer's body after swelling and prevent sagging of the diaper article (10). The absorbent layers may be disposed in plurality in the absorbent core (621, 622).

Alternatively, the absorbent core (621, 622) may comprise a high loft material encompassing superabsorbent polymers. The term "high loft" refers to low density bulky fabrics, as compared to flat, paper-like fabrics. High loft webs are characterized by a relatively high porosity. This means that there is a relatively high amount of void space in which superabsorbent polymer particles can be distributed. The high loft material (without the superabsorbent particles) may have a density at a pressure of 4.14 kPa (0.6 psi) below 0.20 g/cm$^3$, in particular ranging from 0.05 g/cm$^3$ to 0.15 g/cm$^3$. The high loft layer (without the superabsorbent particles) may have a density at a pressure of 2.07 kPa (0.3 psi) below 0.20 g/cm$^3$, in particular ranging from 0.02 g/cm$^3$ to 0.15 g/cm$^3$. The high loft layer (without the superabsorbent particles) may have a density at a pressure of 0.83 kPa (0.12 psi) below 0.15 g/cm$^3$, in particular ranging from 0.01 g/cm$^3$ to 0.15 g/cm$^3$, and a basis weight of from 15 to 500 gsm, preferably 30~200 gsm, such as those described in US 2021/0361497 A1. The absorbent core (621, 622) comprising high loft material encompassing superabsorbent polymers may also contain channels.

The absorbent cores (621, 622) may also contain an acquisition system for facilitating the acquisition and the distribution of body exudates, and may be placed between the topsheet (241, 242) and the absorbent layer. The function of the acquisition system is to rapidly acquire the fluid from the topsheet (241, 242) away from the wearer-facing side and/or to distribute over a larger area so it is more efficiently absorbed by the absorbent core. The acquisition system may include cellulosic fibers. Channels may also be formed in the acquisition system, and may be configured to at least partly match the channels of the absorbent layer in the thickness direction. It is also possible that such another liquid management layer may be placed between the backsheet (251, 252) and the absorbent layer. The liquid management layer may be a spunlace nonwoven comprising viscose, PET, CoPET/PET fibers, and combinations thereof.

Dimensions

Referring to FIGS. 2A, 2B, and 3, the components for forming the absorbent assembly (20) may have a particular relationship with one another for ensuring that the second absorbent body (39) remains intact during the first usage, while maintaining wear comfort and enabling smooth removal of the first absorbent body (38) after usage. Hereinafter, it is defined that the first backsheet (251) has a transverse dimension T1 and a longitudinal dimension L1, the first outer cover (421) has a transverse dimension T2 and a longitudinal dimension L2, the second topsheet (242) has a transverse dimension T3 and a longitudinal dimension L3, and the chassis backsheet (252) has a transverse dimension T4 and a longitudinal dimension L4. The substrate elements of the absorbent assembly (20) are all depicted in rectangles in FIGS. 2A and 2B. Alternatively, the 4 edges of the elements of the absorbent assembly (20), and particularly elements of the first absorbent body (38), may be rounded off such as in FIGS. 1A-1B and 7A-7F. Such rounding off may be beneficial for avoiding the first absorbent body (38) having sharp edges, which sharp edges may otherwise be well observed during the removing activity by the wearer or caregiver (hereinafter collectively "user"). For purpose of determination of dimensions T1, T2, T3, T4, L1, L2, L3, and L4, the maximum transverse dimensions and maximum longitudinal dimensions of each element is measured.

The Temporary Bond (TB) for bonding the first and second absorbent bodies (38, 39) is provided between the first outer cover (421) and the second topsheet (242) such that the first absorbent body (38) may be removed from the remainder of the diaper article (10) after first usage. In order not to soil the second absorbent body (39) during first usage, T1 is provided greater than T3, preferably T1 may be provided greater than T3 by from about 5 mm to about 15 mm. Further, T2 may be provided greater than T3 for the same purpose, preferably T2 may be provided greater than T3 by from about 5 mm to about 45 mm.

Referring to FIG. 3, the first absorbent body (38) may further comprise a first outer cover fold over (43) connected to the first outer cover (421), wherein the transverse edges of the first backsheet (251) is sandwiched by the first outer cover (421) and the first outer cover fold over (43). By providing the elements of the first absorbent body (38) in such configuration, there is provided improved protection along the transverse edges of the absorbent assembly (20), and visual exposure of the first backsheet (251) to the user may be avoided. Visual exposure of the backsheet (251, 252) is typically avoided for the purpose of providing the article a finished appearance, and also for avoiding exposure of color of exudates after soiling of the absorbent assembly (20). For purpose of determination of dimension T2, only the first outer cover (421) is concerned, and the dimension of the first outer cover fold over (43) is not counted.

Referring to FIGS. 2A and 2B, L3 may be provided greater than L1, preferably L3 may be provided greater than L1 by from about 20 mm to about 60 mm. Namely, the front end and/or the back end of the second topsheet (242) may be extended beyond the first backsheet (251) as well as the first outer cover (421). By providing the first absorbent body (38) and the second absorbent body (39) in such configuration, the user may conveniently remove the first absorbent body (38) from the remainder of the absorbent assembly by inserting fingers between the first outer cover (421) and the second topsheet (242). The chassis backsheet (252) provides barrier function for the entire diaper article (10). In order to provide such function, T4 may be greater than T1, preferably T4 may be provided greater than T1 by from about 40 mm to about 60 mm. T4 may be provided greater than any of T1, T2, or T3. L4 may be greater than L1 or L2. The first absorbent core is provided smaller in dimension than T1, T2, L1, and L2. The second absorbent core is provided smaller in dimension than T3, T4, L3, and L4. For purpose of clarification, in FIG. 3, T2 is shown in greater dimension than T1 due to the exaggeration of the thickness of the first outer cover (421) thus adding dimension at the left and right folding points. In reality, however, the embodiment described in FIG. 3 has T1 and T2 in the same transverse dimension.

Still referring to FIGS. 2A and 2B, the absorbent core existing on the garment facing side, namely the second absorbent core (622), may have the distance between the front end of the core and the front end of the absorbent assembly (20) shorter than the distance between the back end of the core and the back end of the absorbent assembly (20). By somewhat shifting the core towards the front than in the longitudinal center, the absorbent core may effectively receive and absorb fluid waste. When the second absorbent core (622) is disposed at such position relative to the absorbent assembly (20), the back end of the first and second absorbent cores (621, 622) may be matched, while the front end of the first absorbent core (621) exists proximal from the front end of the second absorbent core (622). By providing the first and second absorbent cores (621, 622) in such position, the vicinity of the longitudinal edge of the first outer cover (421) on the front side may be kept thin by being devoid of the first absorbent core (621), thus facilitating inserting fingers between the first outer cover (421) and the second topsheet (242) for the removing activity of the first absorbent body (38). Such longitudinal dimension difference of the first and second absorbent cores (621, 622) may be provided on the front side, where there is remained less longitudinal dimension between the front end of the absorbent cores (621, 622) and the absorbent assembly (20).

Temporary Bond

The absorbent assembly (20) of the present invention has the first outer cover (421) and the second topsheet (242) bonded with a Temporary Bond (TB) for enabling removal of the first absorbent body (38) from the remainder of the diaper article (10), after the first use. The Temporary Bond (TB) is provided between two nonwoven layers, the first outer cover (421) and the second topsheet (242) with an appropriate peeling strength. The Temporary Bond (TB) may be provided by any of adhesive, heat energy, ultrasonic energy, or combinations thereof. The Temporary Bond (TB) may have a Peak Force of about 16N or lower, or a Peak Force of from about 4N to about 15N, or a Peak Force of from about 4N to about 10N, or a Peak Force of from about 6N to about 15N, or a Peak Force of from about 10N to about 15N, and an Average Force of about 0.3N or higher, or an Average Force of from about 0.4N to about 15N, or an Average Force of from about IN to about 15N, or an Average Force of from about 0.4N to about 14N, according to the Peel Strength Measurement herein. The Peel Strength Measurement herein intends to mimick the removing activity of the user when the first absorbent body (38) is removed from the remainder of the diaper article by starting the breaking of the Temporary Bond (TB) from either of the front or back end of the first absorbent body (38) towards the other of the front or back end. The Average Force resembles the force observed during the middle of the removing activity. By having an Average Force of about 0.3N or higher, the Temporary Bond (TB) is strong enough to endure the forces created during the first usage by the wearer. The Peak Force resembles the maximum force experienced during the removing activity. By having a Peak Force of about 16N or lower, the Temporary Bond (TB) is weak enough that the bond may be broken without significant effort and without destroying other components of the diaper article (10).

So long as the above mentioned Peak Force and Average Force according to the Peel Strength Measurement herein are achieved, the first outer cover (421) and the second topsheet (242) may be any nonwoven material suitable for use as a diaper article (10). Exemplary first outer cover (421) materials may be selected from those having a basis weight of from about 6.5 gsm to about 25 gsm, preferably from about 8 gsm to about 20 gsm. Exemplary second topsheet (242) materials may be selected from those having a basis weight of from about 11 gsm to about 40 gsm, preferably from about 15 gsm to about 40 gsm. The first outer cover (421) may have a lower basis weight than that of the second topsheet (242).

Figure 4C:
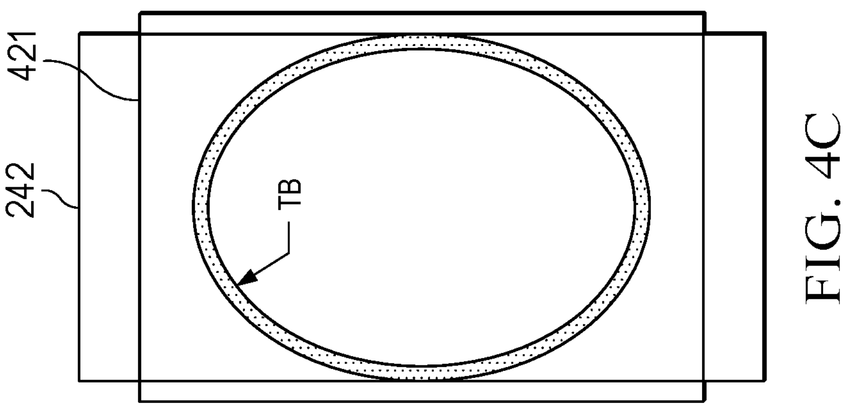
FIGS. 4A-4C are schematic plan views of embodiments of Temporary Bonds of the present invention.
Figure 4B:
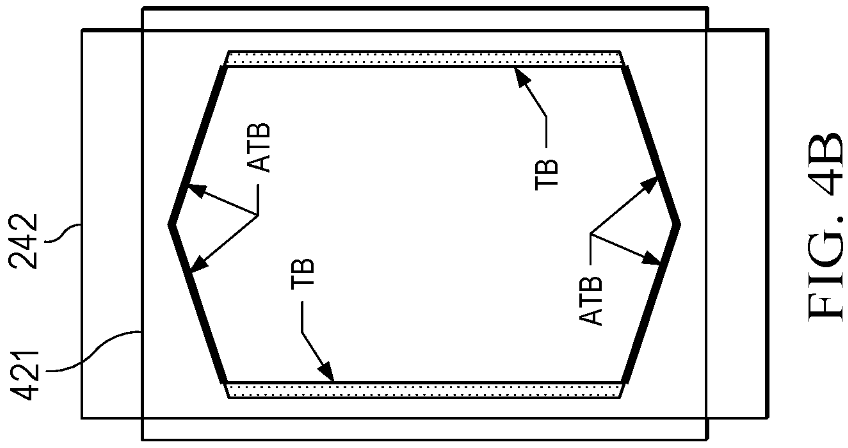
Figure 4A:
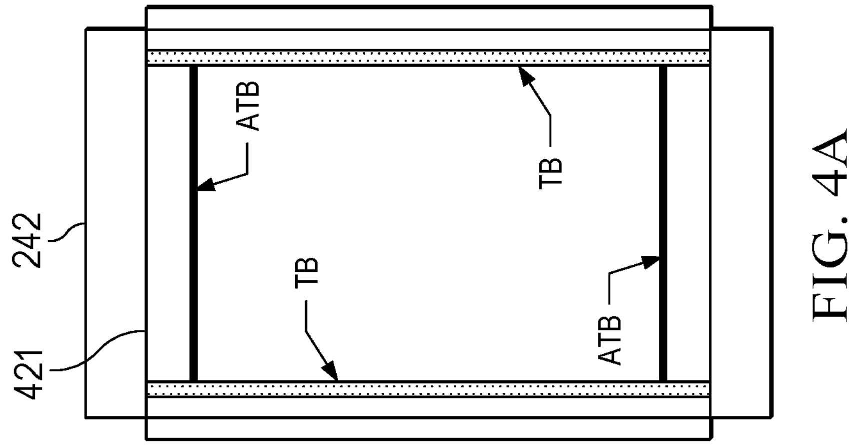

FIGS. 4A-4C are schematic plan views of embodiments of Temporary Bonds (TB) of the present invention. The Temporary Bonds (TB) may be provided at least partially along the transverse edges of the second topsheet (242) and extending in the longitudinal direction. As in FIGS. 4A-4B, the Temporary Bonds (TB) may be a substantially straight line along the left and right transverse edges of the second topsheet (242). Alternatively, as in FIG. 4C, the Temporary Bond (TB) may be a continuous line, such as in oval shape, extending along at least partially the transverse edges of the second topsheet (242). The continuous line may be in the shape of rectangle, or other polygon.

Referring to FIGS. 2A, 2B and 4A-4C, the first outer cover (421) comprises a front longitudinal edge region within about 5 mm from the front end of the first outer cover (421) and within about one third of the transverse dimension of the first outer cover (421) from the longitudinal axis. The first outer cover (421) comprises a back longitudinal edge region within about 5 mm from the back end of the first outer cover (421) and within about one third of the transverse dimension of the first outer cover (421) from the longitudinal axis. The Temporary Bond (TB) may be devoid in the front and back longitudinal edge regions. Referring to FIG. 4A, the Temporary Bond (TB) may extend in the longitudinal direction up to the front and back ends of the first outer cover (421). Referring to FIG. 4B, the Temporary Bond (TB) may extend in the longitudinal direction, however, leaving the front and back ends of the first outer cover (421) unbonded. By providing the Temporary Bond (TB) devoid in the front and back longitudinal edge regions, this facilitates inserting fingers between the first outer cover (421) and the second topsheet (242) for starting the removing activity.

Still referring to FIGS. 4A-4B, there may further be provided an Auxiliary Temporary Bond (ATB) between the first outer cover (421) and the first outer cover (421), wherein the Auxiliary Temporary Bond (ATB) provides the same or lower Peak Force as the Temporary Bond (TB) according to the Peel Strength Measurement herein. The Auxiliary Temporary Bond (ATB) may be disposed between the Temporary Bonds (TB) extending in the transverse direction, wherein the Auxiliary Temporary Bond (ATB) is devoid in the front and back longitudinal edge regions. The Auxiliary Temporary Bond (ATB) may be connected with the left and right Temporary Bonds (TB). As in FIGS. 4A-4B, the Auxiliary Temporary Bond (ATB) may be disposed adjacent the longitudinal edge regions. Referring to FIG. 4A, the Auxiliary Temporary Bond (ATB) may be a straight line extending in the transverse direction. The Auxiliary Temporary Bond (ATB) may be provided in a position of from about 5 mm to about 40 mm away from the front and back longitudinal edges of the first outer cover (421). By providing the Auxiliary Temporary Bond (ATB) in this position, there is enough space for the user to insert fingers between the first outer cover (421) and the first outer cover (421), for starting the removing activity, while not leaving too much unbonded area. When there is left much unbonded area towards the front and back longitudinal ends of the first absorbent body (38), this may lead to unnecessary folding. Referring to FIG. 4B, the Temporary Bond (TB) may be a curvature with the concave portion facing the front or back end and extending in the transverse direction. The Auxiliary Temporary Bond (ATB) may be provided in a position wherein the concave portion closest to the front or back end is from about 5 mm to about 40 mm away from the front and back longitudinal edges of the first outer cover (421).

Figure 7A:
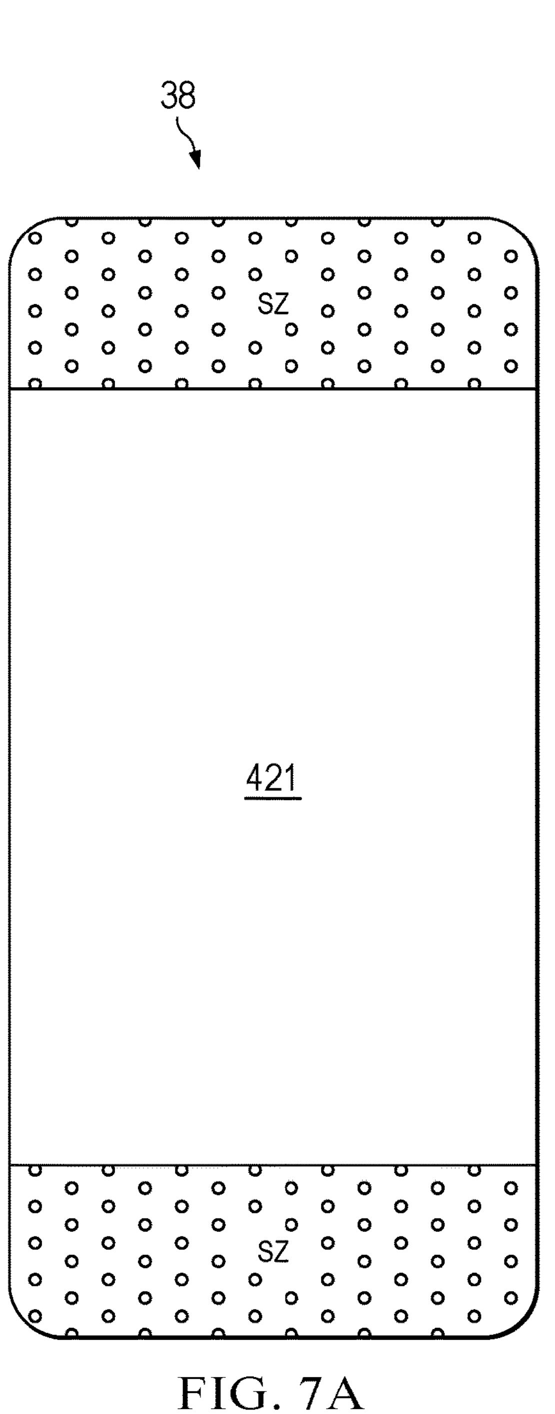
FIGS. 7A-7F are schematic plan views of embodiments of Signal Zones of the present invention.
Figure 7B:
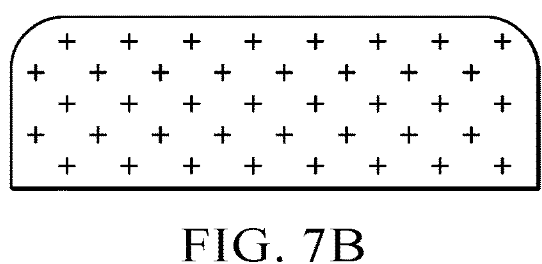
Figure 7C:
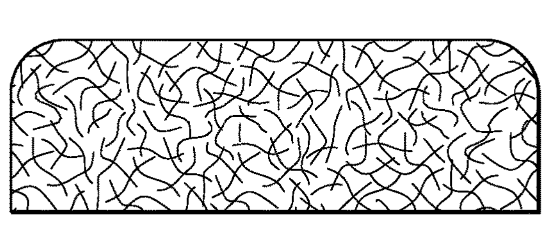
Figure 7D:
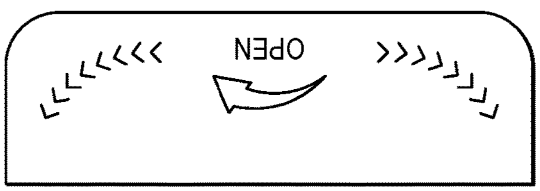
Figure 7E:
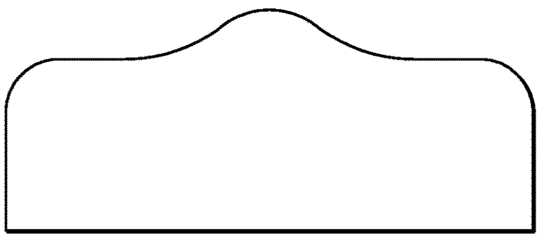
Figure 7F:
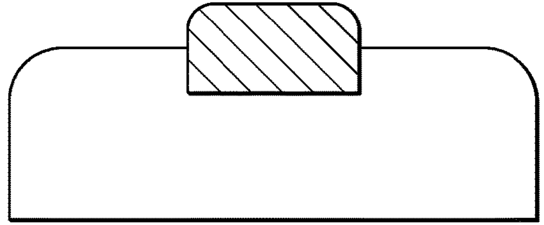

Referring to FIGS. 1B and 7A, the garment facing side of the first absorbent body (38), namely the first outer cover (421), may be provided with a Signal Zone (SZ) which includes an indicia for intuitively guiding the user where the first absorbent body (38) may be pinched for effectively starting the removing activity of the first absorbent body (38) from the remainder of the diaper article (10). The Signal Zone (SZ) may be provided adjacent the front and/or back ends of the first outer cover (421), and may overlap the front or back longitudinal edge region of the second topsheet (242). It may be advantageous to provide the Signal Zone (SZ) adjacent the front end of the first outer cover (421) to guide the user to start the removing activity from the front side, as being relatively more hygienic than starting the removing activity from the back side. It may be advantageous to provide the Signal Zone (SZ) adjacent the front end of the first outer cover (421) to guide the wearer oneself to start the removing activity from the front side in a seated posture. It may be advantageous to provide the Signal Zone (SZ) adjacent the back end of the first outer cover (421) to guide the caregiver to start the removing activity from the back side, as being convenient for starting the removing activity when the wearer is in a standing posture. It may be advantageous to provide the Signal Zone (SZ) both adjacent the front end and the back end of the first outer cover (421) to enable the user to start the removing activity according to various habits as mentioned above or otherwise. It may be advantageous to provide the Signal Zone (SZ) both adjacent the front end and the back end of the first outer cover (421) to enable the caregiver to remove the first absorbent body (38) from both the front and back side upon diaper change when the wearer is in a lying posture. Referring to FIGS. 7B-7D, the indicia may be a color and/or pattern distinguishable from the remainder of the first outer cover (421), a material and/or topography distinguishable from the remainder of the first outer cover (421), wording such as "open", "start peel" and/or combined with signals such as arrows. Any of the indicia of FIGS. 7B-7D may be provided in printing, physical treatment such as embossing, quilting, openings or heating, by attaching an additional material, or any combination thereof. Referring to FIG. 7E, indicia may be provided by altering the shape of the Signal Zone (SZ), for example, by providing a projection in the transverse center. Such altered shape of the first outer cover (421) may optionally be matched with other material of the first absorbent body (38), such as the first topsheet (241), and/or the first backsheet (251). Referring to FIG. 7F, indicia may be provided by attaching an additional material to the Signal Zone (SZ) which additional material projects out from the first outer cover (421). The indicia of any of FIGS. 7B-7F may be combined with each other.

Other Components

The absorbent assembly (20) of the present invention may further comprise components that improve leakage prevention, wearability, fit, or aesthetic aspects of the resulting diaper article (10).

Referring to FIG. 3 and FIGS. 2A and 2B below TX, the chassis (20) may further comprise components that improve the fit of the diaper article around the legs of the wearer. A pair of chassis cuffs may be provided along the transverse edges of the chassis and extending in the longitudinal direction. The chassis cuffs may comprise a pair of chassis inner cuffs (31) and a pair of chassis outer cuffs (34). The chassis inner cuffs (31) may be formed by a piece of material, typically a nonwoven, which is partially bonded to the chassis backsheet (252) and can be partially raised away and thus stand up from the plane defined by the first topsheet (241). The chassis inner cuffs (31) have a free terminal edge intended to contact and form a seal with the wearer's skin. The standing up portion of the inner cuffs (31) typically comprise an elastic element, for example one or a plurality of clastic bodies (35). The chassis inner cuffs (31) provide improved containment of liquids and other body exudates approximately at the junction of the torso and legs of the wearer. In addition to the chassis inner cuffs (31), the article may comprise chassis outer cuffs (34), which are formed in the same plane as the chassis backsheet (252) which may be at least partially enclosed between the material for forming the chassis inner cuffs (31) and the chassis backsheet (252), and may be placed transversely outwardly relative to the chassis inner cuffs (31). The chassis outer cuffs (34) can provide a better seal around the thighs of the wearer. The chassis outer cuffs (34) may also comprise one or a plurality of elastic bodies (33). Comparing the upper and lower portions divided by TX of each of FIGS. 2A and 2B, the material for forming the chassis outer cuffs (34) covers the portion of the chassis backsheet (252) which may otherwise be exposed. As explained above, there is benefit in avoiding exposure of the backsheet to the user, as this provides a finished appearance. Referring to FIG. 3, the chassis outer cuffs (34) may be formed by the chassis backsheet (252), a chassis cuff material, and a plurality of outer cuff elastic bodies (33) sandwiched between the chassis backsheet (252) and the chassis cuff material, and wherein the chassis inner cuffs (31) may be formed by the same chassis cuff material for forming the chassis outer cuffs (34) extending inwardly and encompassing a plurality of inner cuff elastic bodies (35).

Figure 6A:
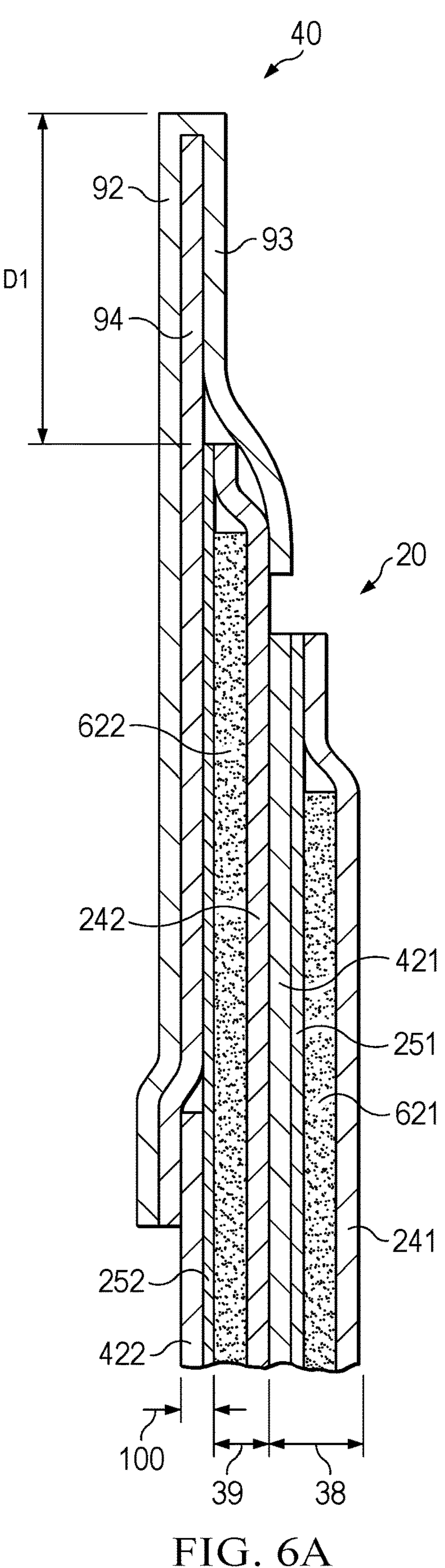
FIG. 6A is an embodiment of a longitudinal schematic cross section view of FIG. 5B taken along the longitudinal axis LX having the absorbent assembly of FIG. 2A, and with the Temporary Bond and elastic bodies abbreviated.
Figure 6B:
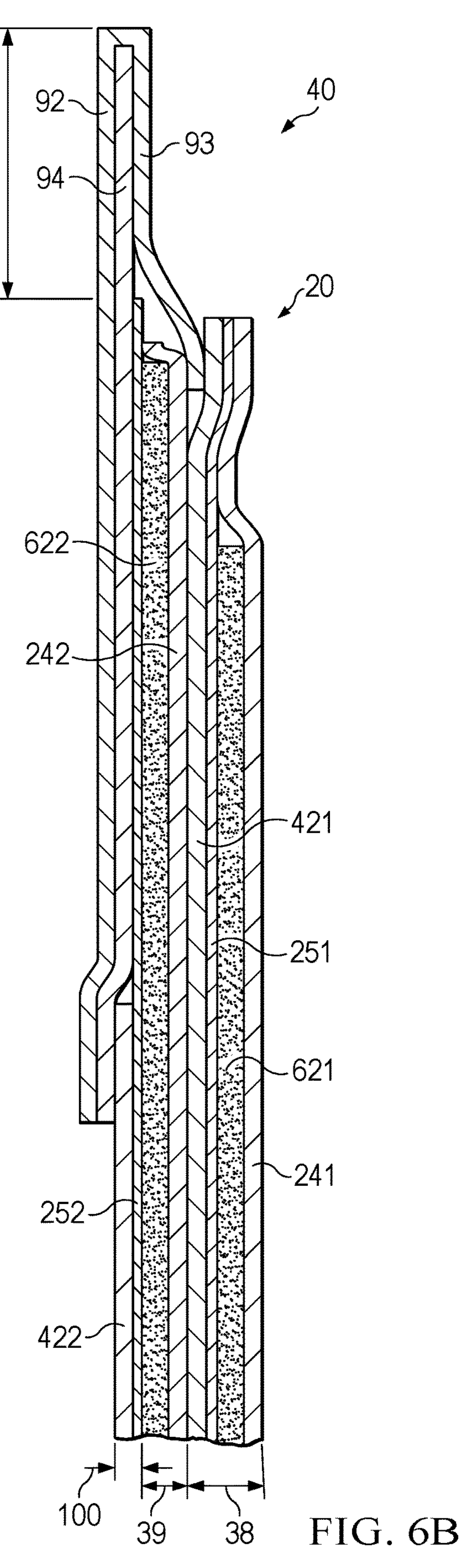
FIG. 6B is another embodiment of a longitudinal schematic cross section view FIG. 5B taken along the longitudinal axis LX having the absorbent assembly of FIG. 2B and with the Temporary Bond and elastic bodies abbreviated.

Referring to FIG. 2A towards the front and back ends, the second topsheet (242) may extend in the same dimension as the chassis backsheet (252) such that there is no area of the chassis backsheet (252) exposed towards the front and back ends of the absorbent assembly (20). Alternatively, referring to FIG. 2B towards the front and back ends, there may be a small area extending in the longitudinal dimension from the front and back ends of the absorbent assembly (20) where the chassis backsheet (252) is exposed. Referring to FIG. 6B, when the diaper article is a pant type, such area otherwise exposed may be covered by the outer sheet fold over (93). While not shown, when the diaper article is a taped type, such area otherwise exposed may be covered by a waist band attached along the front and back ends of the absorbent assembly (20) extending in the transverse direction, and having elasticity in the transverse direction.

As is typically provided for diaper articles with a single absorbent body, the chassis backsheet (252) and/or the chassis outer cover (422) may be provided with artwork which may be visible from the garment facing side of the diaper article (10). Such artwork may be coordinated with artwork provided on the fastening structure, for example the elastic belts, for forming a pant article.

The first absorbent body (38) and the second absorbent body (39) may be provided with different aesthetics discernible from the topsheet side so that the user may distinguish between the first and second absorbent body (38, 39), and/or for appealing the existence of multiple absorbent bodies. For example, the first and second topsheets (241, 242) may be provided with different topography such as bondings, embossings, and openings. For example, the adhesive for bonding the first or second topsheet (241, 242) with layers directly underneath may be provided in a color and a pattern, wherein the color and/or pattern provided in the first and second absorbent body (38, 39) may be different.

Pant Diaper Article

Figure 5B:
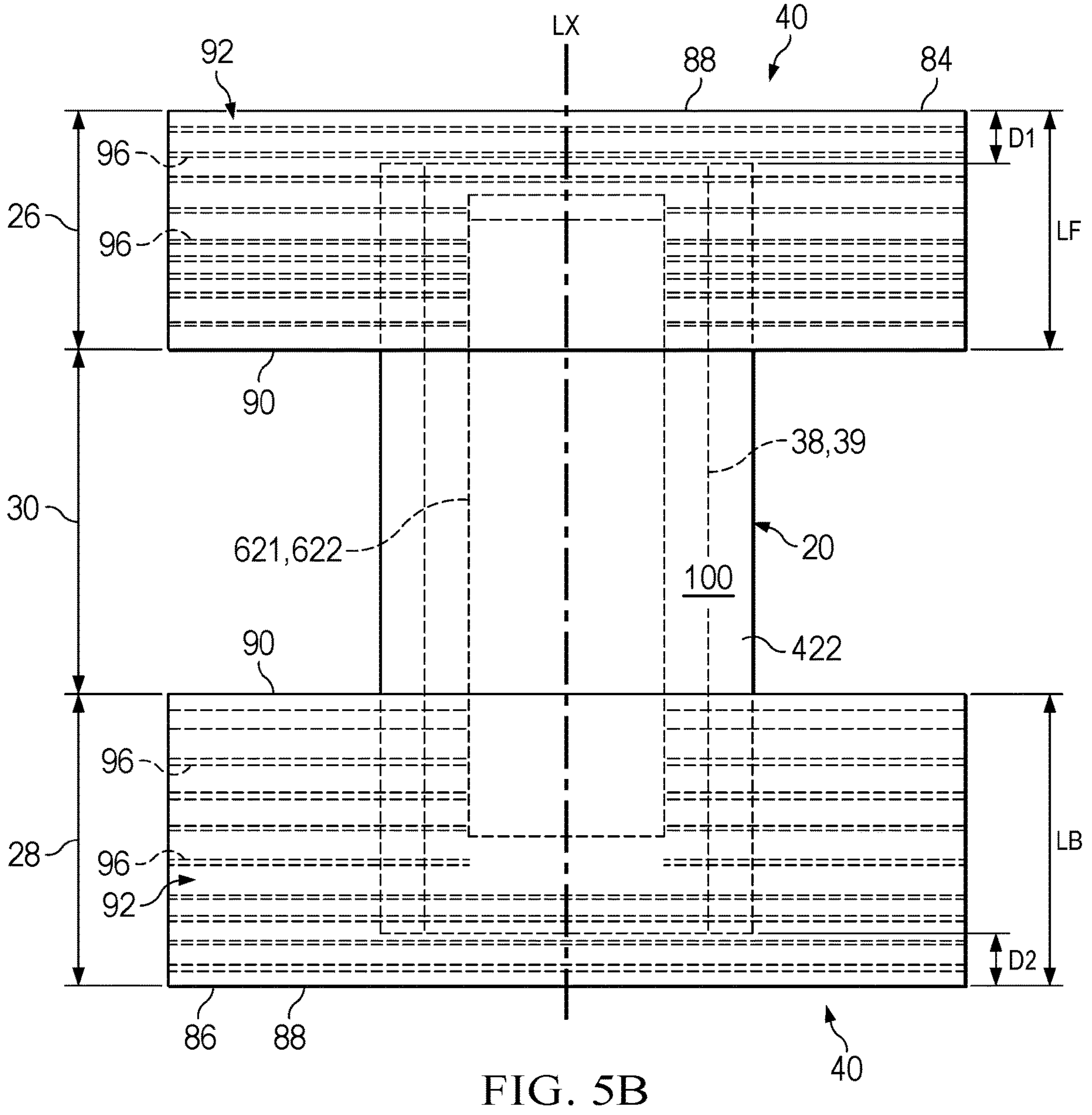
FIG. 5B is a schematic plan view of an embodiment of a pant diaper article of the present invention with the seams unjoined and in a flat uncontracted condition showing the garment facing surface.

Referring to FIGS. 5A and 5B, the diaper article (10) of the present invention may be in the pant form wherein the application structure (40) is an elastic belt (40), the elastic belt (40) comprising a front belt (84), a back belt (86), and a pair of side seams (32) sealing the transverse edges of the front belt (84) and the back belt (86). The pant diaper article (10) may be a belt-type pant as in FIGS. 5A and 5B wherein the front belt (84) and the back belt (86) are discontinuous in the longitudinal direction, and assembled with the absorbent assembly (20) wherein the front and back belts (84, 86) are positioned on the garment facing side of the absorbent assembly (20), wherein by the side seam (32) sealing the front and back belts (84, 86) form a ring-like belt. For the belt-type pant, the front belt (84) may be referred to as the front region (26), the back belt (86) may be referred to as the back region (28), and the remainder may be referred to as the crotch region (30). The front and back belts (84, 86) may be rectangular. At least one of the front and back belts (84, 86) may be shaped (not shown). For the belt-type pant, the longitudinal dimension (LB) of the back belt (86) may be greater than that (LF) of the front belt (84), wherein the distal edges (88) of the front belt (84) and the back belt (86) are matched for seaming, thereby leaving the proximal edges (90) of the back belt (86) remaining unsealed. The unsealed proximal edges of the back belt (86) may form a buttock cover. While not shown, the pant elastic article (10) may be a one-piece type wherein the front and back belt (86) are continuous.

Referring to FIG. 5B, the front belt (84) and the back belt (86) may each be formed by a laminate comprising a plurality of elastic bodies (96) running in the transverse direction. At least some of the elastic bodies (96) extend in the transverse direction substantially parallel to each other. Referring to FIGS. 5B, 6A and 6B, the front belt (84) and the back belt (86) may each comprise a laminate, the laminate comprising a plurality of elastic bodies (96) running in the transverse direction, an inner sheet (94), an outer sheet (92), and an outer sheet fold over (93) wherein the outer sheet fold over (93) is an extension of the outer sheet material formed by folding the outer sheet material at the distal edge (88) of the front and back belts; wherein the elastic bodies (96) are sandwiched between two of these sheets. The outer sheet fold over (93) from the front and back belts (84, 86) may sandwich the front and back longitudinal edges of some components of the absorbent assembly (20). The front elastic belt (84) and the back elastic belt (86) may each be made only by elastic bodies (96), the inner sheet (94), the outer sheet (92), and the outer sheet fold over (93). The clastic bodies (96) may be disposed in the same or different denier, interval, and force between the front and back, as well as in different longitudinal positions of the belt.

Referring back to FIG. 5B, the pant diaper article (10) is formed by the absorbent assembly (20), the front belt (84) and the back belt (86), wherein the position of the absorbent assembly (20) in view of the front belt (84) and back belt (86) are arranged in order to provide good absorbency as well as good wear comfort. When the pant diaper article (10) has the seams unjoined and in a flat uncontracted condition of the clastic members, the side seam and the diaper article (10) each have a longitudinal dimension. When the longitudinal dimension (LB) of either belt is greater than that (LF) of the other belt, the longitudinal dimension of the side seam equals LF. When the pant diaper article (10) has the seams unjoined and in a flat uncontracted condition of the elastic members, the longitudinal dimension between the proximal edge of the front side seam and the proximal edge of the back side seam, may be from about 40% to about 70%, preferably from about 43% to about 60% of the longitudinal dimension of the diaper article (10). By providing the pant diaper article (10) in such configuration, the absorbent assembly (20) may be appropriately placed against the wearer for wear comfort.

When the diaper article (10) is the belt-type pant as in FIG. 5B, the distal edge of the front belt (84) and the front longitudinal end of the absorbent assembly (20) has a distance D1, and the distal edge of the back belt (86) and the back longitudinal end of the absorbent assembly (20) has a distance D2, D1 may be provided smaller than D2. By providing D1 smaller than D2, the absorbent assembly (20) may be shifted toward the front, thereby effectively receiving and absorbing fluid waste.

Referring to FIGS. 6A and 6B, the pant diaper article (10) of the present invention may have a chassis outer cover (422) provided on the garment facing side of the chassis backsheet (252). The chassis outer cover (422) may be any nonwoven material suitable for the first outer cover (421) mentioned above. When the diaper article (10) is the belt-type pant as in FIG. 5B and a chassis outer cover (422) is present, the chassis outer cover (422) may extend through the crotch region (30) but only partly in the longitudinal direction in the front and back regions (26, 28) to leave the distal parts of the front belt (84) and the back belt (86) free of the chassis outer cover (422). Namely, the longitudinal length of the chassis outer cover (422) may be longer than the distance between the front and back belts (84, 86), and shorter than the longitudinal length of the chassis backsheet (252). By such configuration, the distal parts of the front belt (84) and the back belt (86) are devoid of the chassis outer cover (422), thereby provide the overall article (10) relatively thin, and provide cost saving.

As described above, it may be advantageous to guide the user to start the removing activity of the first absorbent body (38) from the front and/or back end of the first absorbent body (38). Referring to the front side, the longitudinal dimensions of the components of the absorbent assembly (20) may be coordinated with the components of the front belt (84) for accommodating the removing activity. Referring to FIGS. 2A and 6A, the outer sheet fold over (93) may be provided in a dimension such that the front longitudinal edges of components of the second absorbent body (39) as well as the chassis (100) may be sandwiched between the inner sheet (92) and the outer sheet fold over (93), while the front longitudinal edges of components of the first absorbent body (38) exist proximal from the proximal edge of the outer sheet fold over (93). Alternatively, referring to FIGS. 2B and 6B, the front longitudinal edges of components of the first absorbent body (38) may exist distal from the proximal edge of the outer sheet fold over (93), and provided on the wearer-facing side of the outer sheet fold over (93). In either configuration of FIG. 6A or 6B, the removing activity of the user may be accommodated. While not shown, the longitudinal dimensions of the components of the absorbent assembly (20) may be coordinated with the components of the back belt (86) in similar configuration as described above for the front side.

Peeling Strength Measurement Method

1. Preparation of Finished Product Specimen

Specimen for the measurements hereinbelow is obtained from 3 finished diaper article samples. When the article is a pant, peel apart the side seam of the pant. The article is then stretched in the longitudinal direction such that any longitudinally extending elastic bodies, such as cuff elastics, are fully stretched, and then the article is attached on an appropriate board having at least an area of the fully stretched article via any attachment means, such as tape, adhesive, hooks, or the like. Identify which of the front or back side ("peeling side") the first absorbent body is intended to be peeled off from the remainder of the article. Cut by scissors along the width direction (transverse direction) at 10 cm from the longitudinal edge of the first absorbent body on the peeling side by scissors. The portion exposed by such cutting is the measurement edge.

2. MTS Test Setting and Measuring

As equipment, MTS Criterion Model 42 running TW Elite 4.3.1.375 software with standard tensiometer or equivalent is used. All testing is performed in a room maintained at 23±2° C. and 50±5% relative humidity.

The initial distance between the upper grip and lower grip is set to be 20 mm. Grips having a transverse dimension greater than the width of the Temporary Bonding on the left and right sides are selected, such that the specimen is peeled at the same horizontal level simultaneously. The measurement edge of the specimen is gripped by the grips such that the upper grip is clamping the first absorbent body, and the lower grip is clamping the remainder of the article. The specimen is set such that the transverse direction of the specimen matches the horizontal direction of the equipment. A constant rate of extension of 500 mm/min is applied. The elongation measurement is taken from the point where the program starts. The upper grip starts moving up, while the lower grip remains static, resulting in the first absorbent body's peeling off. The program stops until the upper grip moves 200 mm. The force (N) is continuously measured by the machine at a sampling rate of 50 Hz.

The Peak Force is the maximum force value observed during the measurement process. The Average Force is the average value observed between 80 mm and 160 mm extension. For both values, measurements from 3 specimens are obtained and averaged up to 0.01N preciseness.

Folded Thickness Measurement Method

1. Preparation of Finished Product Specimen

Specimen for the measurements hereinbelow is obtained for 3 finished diaper articles. When the article is a pant, the article is used in its original form. When the article is a taped diaper, the article is folded in half along the longitudinal center line of the article. The folded longitudinal center of the article is called the "bottom".

2. Folded Thickness Measurement

As equipment, Ono Sokki Closed Shaft foot caliper with 24.13 mm diameter foot exerting 0.689 kPa on Ames stand with Caliper Gauge GS-503 or equivalent; Digital Readout DG-3610 Measure all or equivalent are used. All testing is performed in a room maintained at 23±2° C. and 50±5% relative humidity.

The specimens are obtained immediately after they are removed from a freshly opened package, and subject to the following measurement, such that measurement may be completed in 5 minutes from opening the package:

(1) Lift the caliper foot carefully by hand, lay the specimen flat on the caliper stand and place the caliper foot on the specimen such that the caliper foot is placed 5 mm away from the bottom, and at the transverse center. Wait approx. 5 seconds and take the reading. The reading is the thickness of the bottom of the article.

(2) Lift the caliper foot carefully by hand, lay the specimen flat on the caliper stand and place the caliper foot on the specimen such that the caliper foot is placed 50 mm away from the bottom, and at the transverse center. Wait approx. 5 seconds and take the reading. The reading is the thickness of the bottom of the article.

(3) The value obtained by steps (1) and (2) are averaged.

The Folded Thickness is the average of the value obtained in (3) from 3 samples averaged up to 0.1 mm preciseness.

EXAMPLE

Examples 1-2 and Comparative Examples 1-2 are Size 4 (L-size) belt-type pant diaper articles having 2 absorbent bodies and with configuration of FIGS. 2A, 3, 4A, 5B, and 6A, and the dimensions of Table 1 below. Examples 1-2 have Peak Force, Average Force, and Folded Thickness as in Table 2 below.

TABLE 1

| Venue | Examples 1, 2 | Comparative Example 1 | Comparative Example 2 |
|---|---|---|---|
| T1 (mm) | 150 | 140 | 150 |
| T2 (mm) | 150 | 140 | 150 |
| T3 (mm) | 140 | 150 | 140 |
| T4 (mm) | 198 | 198 | 140 |
| L1 (mm) | 370 | 370 | 370 |
| L2 (mm) | 370 | 370 | 370 |
| L3 (mm) | 403 | 403 | 403 |
| L4 (mm) | 403 | 403 | 403 |

The pant diaper article of Examples 1-2 provide two layers of absorbent bodies for two usages wherein the absorbent body for second usage remains intact during the first usage. The pant diaper article of Comparative Example 1 having T3 greater than T1 risks leakage of bodily exudates to the second absorbent body while usage of the first absorbent body. The pant diaper article of Comparative Example 2 having T4 smaller than T1 risks leakage of bodily exudates from the overall article during either the first or second usage.

TABLE 2

| Venue | Example 1 | Example 2 |
|---|---|---|
| Peak Force (N) | 7.17 | 12.71 |
| Average Force (N) | 3.40 | 1.49 |
| Folded Thickness (mm) | 11.2 | 11.2 |

The Temporary Bonds of pant diaper article of Examples 1-2 endure the forces created during the first usage by the wearer, and are capable of being broken without destroying other components of the pant diaper article. The pant diaper article of Examples 1-2 appear and feel thin enough to the consumer as an article on the market with single absorbent body.

Consumer Acceptance 12 panelists in Nanjing, China who were users of similar price range products as the target consumers were recruited. They were asked to use the products they used most often (hereinafter "benchmark") for 2 days, and then to use pant diaper article samples of Example 1 (hereinafter "Example 1") for 2 days, and answer a set of questions. Table 3 shows results of the panelists scoring each sample in a scale of 0 to 100 points against the attribute of "easy application". Table 4 shows results of percentage of panelists who "strongly agreed" or "somewhat agreed" to the statement. Table 5 shows results of percentage of panelists who agreed to the statements.

TABLE 3

| | Example 1 | Benchmark |
|---|---|---|
| Easy application | 73points *1) | 8points |

TABLE 4

| Statement | Example 1 | Benchmark |
|---|---|---|
| The time and effort I spend on diaper change is what I desire for | 83% *1) | 8% |

*1) Statistically significantly better compared to Benchmark at 90% confidence.

TABLE 5

| Statement | |
|---|---|
| It's much easier application compared to Benchmark | 58% |
| It's a little easier application compared to Benchmark | 33% |
| I feel less pressure or less struggle during diaper change | 92% |
| It's the most effortless diaper I have ever experienced | 83% |
| It's a product I'm willing to continue to use for my baby | 92% |
| It's a hygienic product for mom to peel (first absorbent body from remainder of article) | 83% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A diaper article comprising an absorbent assembly and an application structure, the absorbent assembly comprising:

1) A first absorbent body comprising:
   a) a first water permeable topsheet;
   b) a first water impermeable backsheet having a transverse dimension T1;
   c) a first absorbent core disposed between the first topsheet and the first backsheet;
   d) a first outer cover disposed on a garment facing side of the first backsheet;
2) a second absorbent body disposed on a garment facing side of the first absorbent body, comprising:
   a) a second water permeable topsheet having a transverse dimension T3;
   b) a second absorbent core; and 3) A chassis disposed on a garment facing side of the second absorbent core, the chassis comprising a water impermeable chassis backsheet;

wherein the first absorbent body further comprises a first outer cover fold over connected to the first outer cover, wherein transverse edges of the first backsheet are sandwiched by the first outer cover and the first outer cover fold over; wherein T1 is greater than T3, and wherein the first outer cover and the second topsheet are bonded by a temporary bond which enables removal of the first absorbent body from a remainder of the diaper article.

2. The diaper article of claim 1 wherein the first outer cover has a transverse dimension T2, wherein T2 is greater than T3.

3. The diaper article of claim 1 wherein the chassis backsheet has a transverse dimension T4, wherein T4 is greater than T1.

4. The diaper article of claim 1 wherein the temporary bond is disposed along transverse edges of the second topsheet extending in a longitudinal direction.

5. The diaper article of claim 1 wherein the first backsheet has a longitudinal dimension L1, and the second topsheet has a longitudinal dimension L3, wherein L3 is greater than L1.

6. The diaper article of claim 5 wherein the second topsheeet comprises a front longitudinal edge region within about 5 mm from a front end of the first outer cover and within about one third of a transverse dimension of the first outer cover from a longitudinal axis, and a back longitudinal edge region within about 5 mm from a back end of the first outer cover, and within about one third of the transverse dimension of the first outer cover from the longitudinal axis, wherein the front and back longitudinal edge regions are devoid of the temporary bond.

7. The diaper article of claim 6 further comprising an auxiliary temporary bond, wherein the auxiliary temporary bond is disposed between at least two temporary bonds and extend in a transverse direction, wherein the front and back longitudinal edge regions are devoid of the auxiliary temporary bond.

8. The diaper article of claim 7 wherein the auxiliary temporary bond is disposed adjacent the front and back longitudinal edge regions.

9. The diaper article of claim 1 wherein the chassis further comprises a pair of chassis cuffs provided along transverse edges of the chassis and extending in a longitudinal direction.

10. The diaper article of claim 1 wherein the Temporary Bond has a Peak Force of 16N or less and an Average Force of 0.3N or higher, according to the Peeling Strength Measurement Method.

11. The diaper article of claim 1 wherein the application structure is selected from the group of a fastening structure and an elastic belt.

12. The diaper article of claim 11 wherein the application structure is an elastic belt comprising a pair of side seams, wherein when the side seams are unjoined and the article is provided in a flat uncontracted condition, a longitudinal dimension between a proximal edge of a front side seam and a proximal edge of a back side seam is from about 40% to about 70% of a longitudinal dimension of the diaper article.

13. The diaper article of claim 12 wherein the elastic belt comprises a front belt and a back belt which are discontinuous with each other in a longitudinal direction and assembled with the absorbent assembly wherein the front and back belts are positioned on a garment facing side of the absorbent assembly, and the chassis comprises a chassis outer cover on a garment facing side of the chassis backsheet, wherein a longitudinal length of the chassis outer cover is longer than a distance between the front and back belts, and shorter than a longitudinal length of the chassis backsheet.

14. The diaper article of claim 13, wherein a longitudinal dimension of the back belt is greater than a longitudinal dimension of the front belt, wherein distal edges of the front belt and the back belt are matched for seaming, thereby leaving the proximal edges of the back belt remaining unsealed, wherein the distal edge of the front belt and a front longitudinal end of the absorbent assembly has a distance D1, the distal edge of the back belt and a back longitudinal end of the absorbent assembly has a distance D2, wherein D1 is less than D2.

* * * * *